United States Patent [19]

Betz

[11] 4,442,856
[45] Apr. 17, 1984

[54] OXYGEN REGULATOR AND ALARM SYSTEM FOR AN ANESTHESIA MACHINE

[75] Inventor: Karl Betz, Dix Hills, N.Y.

[73] Assignee: Puritan-Bennett, Kansas City, Mo.

[21] Appl. No.: 293,993

[22] Filed: Aug. 18, 1981

[51] Int. Cl.³ .......................................... A61M 17/00
[52] U.S. Cl. ..................................... 137/98; 137/539;
128/202.22; 128/203.14; 128/205.24
[58] Field of Search ...................... 137/88, 89, 98, 110,
137/539; 128/203.14, 203.25, 204.21, 204.29,
205.24, 201.27, 201.28, 202.22; 251/120;
138/31, 46

[56] References Cited

U.S. PATENT DOCUMENTS

| | | | |
|---|---|---|---|
| 1,213,652 | 1/1917 | Johnson | 137/539 |
| 2,400,817 | 5/1946 | Fox et al. | 137/539 |
| 3,910,222 | 10/1975 | Metivier | 128/202.22 |
| 4,191,952 | 3/1980 | Schreiber et al. | 128/203.14 |

Primary Examiner—Martin P. Schwadron
Assistant Examiner—James R. Shay
Attorney, Agent, or Firm—Fulwider, Patton, Rieber, Lee & Utecht

[57] ABSTRACT

A low-oxygen alarm regulator assembly including a pair of diaphragms (40, 44) to which oxygen and nitrous oxide pressures are applied, and a displaceable intermediate member (46), the diaphragms having areas inversely proportional to desired flow rate percentages, to maintain the intermediate member in a neutral position if the desired flow ratio is maintained. The intermediate member actuates an alarm if the desired percentage flow of oxygen is not attained. In regulator operation, the assembly employs a valve (10) which is actuated with the alarm to apply an independent flow of oxygen to the oxygen diaphragm and thereby bypass an oxygen flow control valve and maintain a guaranteed oxygen flow ratio. The regulator action can be overriden by operation of a pneumatic switch (98a), which includes various safeguards to preclude inadvertent operation. A variable nitrous oxide flow restrictor 20 compensates for non-linearity in the pressure-flow characteristic for nitrous oxide at very low flows. Also disclosed are an embodiment of the regulator assembly responsive to the ratio between the flow rate of oxygen and the combined flow rates of two other gases and a ventilator alarm for detecting blockages as well as breaks in a patient breathing system is also disclosed.

11 Claims, 19 Drawing Figures

OXYGEN REGULATOR AND ALARM SYSTEM FOR AN ANESTHESIA MACHINE

BACKGROUND OF THE INVENTION

This invention relates generally to gas anesthesia machines, and, more particularly, to alarm and control systems for use in anesthesia machines to ensure that a patient receives an adequate supply of oxygen while undergoing anesthesia, and that the patient is breathing in an uninterrupted breathing cycle.

A gas anesthesia machine includes an oxygen supply, a supply of anesthesia gas, such as a nitrous oxide ($N_2O$) flow control valves and flow meters for the anesthesia gas and the oxygen, and a common outlet by means of which a mixture of the gases is passed to a patient breathing machine. The patient breathing machine, which forms no part of the present invention, is typically a closed-circuit system including a carbon dioxide absorber and at least two check valves, to ensure that the patient inhales gas from the common outlet and exhales through the carbon dioxide absorber. The patient breathing machine may also include a ventilator to pump breathing gas into the patient's lungs, and a gas evacuation system for removal of excess gas from the patient breathing machine.

In simple terms, a gas anesthesia machine provides a mixture of anesthesia gas and oxygen in proportions selected by an operator, who is usually a doctor. The doctor manipulates the flow control valves and monitors the respective flows of the gases through the flow meters. The principal problem with which the present invention is concerned is that the flow of oxygen may inadvertently fall below a danger level, and that the patient may suffer serious physiological damage, or even death, as a result of the oxygen deficiency. The doctor may, for example, become more concerned with increasing the flow of nitrous oxide to further anesthetise the patient, and may not notice that the percentage of oxygen has fallen below the danger level. Various techniques have been devised to provide an alarm indication when the percentage of oxygen falls below a selected level. However, such systems have suffered significant disadvantages, and have provided no means for ensuring that a minimum percentage of oxygen is delivered to the patient.

For example, a low-oxygen alarm device of the prior art is disclosed in U.S. Pat. No. 4,191,952 issued in the name of Schreiber et al. In the Schreiber device, oxygen pressure is applied to one side of a piston and nitrous oxide pressure is applied to the other. By means of springs within the device, and a proper choice of flow restrictors for the two gases, the piston is balanced in a neutral position if the desired proportion of oxygen flow is obtained. If the oxygen flow falls below a selected level, the piston is translated sufficiently in one direction to actuate an alarm switch. One difficulty in devices of this kind is that the spring pressures and flow restrictors must be selected and maintained accurately in order for the device to provide a reliable alarm at the desired flow rate. More significantly, the device does not work well at relatively low flow rates, when the oxygen flow is below one liter per minute.

Flow restrictors in the oxygen and nitrous oxide lines, between the control valves and the flow meters, provide pressures high enough to operate the piston of the device. For the most part, the flow rate through these restrictors increases linearly with the pressure on the supply side of the restrictors. However, nitrous oxide has a distinctly non-linear pressure-flow characteristic at very low flow rates, and the pressure is significantly lower than would be expected if the linear relationship applied. Consequently, at low flows the nitrous oxide restrictor indicates a nitrous oxide flow rate that is lower than the actual flow rate, and the alarm is actuated when the percentage of oxygen is actually much lower than the desired safety level.

A commonly selected minimum safety level is twenty-six percent of oxygen, but for low flows the alarm would be actuated at percentages of oxygen as low as ten percent unless some adjustment or compensation were made to the detector system. In the Schreiber device, the piston is biased in such a manner that, at low flows, the alarm actuation level is higher than twenty-six percent, and sometimes as high as forty percent. While this approach does provide an alarm indication at a conservatively high safety level in low flow conditions, this is not always consistent with what is desired by the doctor. In fact, there may be a tendency for the doctor to switch off the alarm in such conditions, with the consequent risk that the alarm might remain off when a true low-oxygen condition is present at some later time. Ideally, then, the low-oxygen alarm should be actuated consistently at the same selected percentage of oxygen for all flow rates, even down to an extremely low flow rate.

Another significant drawback of the prior art is that the doctor has no way of guaranteeing that a desired proportion of oxygen will be delivered to the patient. In some situations, the alarm might be ignored, or might be malfunctioning for some reason, and the oxygen level could fall substantially below the safety level, unnoticed by the doctor. Thus, there is a real need for a system for controlling the oxygen flow rate to maintain it at or above the selected safety level.

Another important aspect of alarm systems for use in conjunction with gas anesthesia machines is that there should be some means for monitoring the pressure of the gas delivered to the patient. It is common practice in anesthesia machines to employ a pressure sensor located in or near the patient airway or breathing tube, to monitor the variations in airway pressure during successive breathing cycles. When the airway pressure is above a selected threshold value, a pressure-actuated electrical switch is closed, and when the pressure falls below the threshold value the switch opens again. Prior art systems have monitored this type of switch to ensure that successive closures of switches are spaced apart by no more than a preselected time interval. Failure to detect a closure within the time interval results in the actuation of an alarm. This technique reliably detects any break or substantial leak in the breathing system delivering gas to the patient. It does not, however, detect any blockage in the system, since a blockage will keep the switch in a closed condition that will not actuate the alarm.

As will be appreciated from the foregoing, gas anesthesia machines of the prior art have a number of disadvantages in relation to the detection, alarming, and control of undesirable oxygen and breathing gas conditions. The present invention is directed to a solution to these problems.

SUMMARY OF THE INVENTION

The present invention resides in a low-oxygen detection system for use in conjunction with a gas anesthesia machine, wherein the detection system may serve either as an alarm or as part of a control system to maintain the percentage of oxygen flow above a selected level. Briefly, and in general terms, the low-oxygen detection system includes a first diaphragm in a chamber to which oxygen pressure is applied, a second diaphragm in a chamber to which anesthesia gas is applied, and an intermediate member between the two diaphragms, the intermediate member being moved in one direction by action of the oxygen pressure and in the opposite direction by action of the anesthesia gas pressure. To provide the requisite high pressures for actuation of the diaphragms, the oxygen pressure is obtained from the supply side of an oxygen flow restrictor and the anesthesia gas pressure is obtained from the supply side of an anesthesia gas flow restrictor. Importantly, the first diaphragm is approximately three times the area of the second diaphragm so that the pressure of the anesthesia gas needs to be approximately three times the pressure of the oxygen in order for the intermediate member to be held in a neutral position.

Since the gas pressures are approximately proportional to their respective flow rates, the intermediate member will be in the neutral position when the percentage of oxygen flow is approximately twenty-five percent. Because the diaphragms have different areas, the two flow restrictors can be relatively equal in their characteristics and need only be fine-tuned to obtain the desired percentage of oxygen flow. To provide the alarm function of the device, an electrical switch is disposed adjacent to the intermediate member and is actuated when the ratio of the oxygen pressure to the anesthesia gas pressure falls below a preselected value.

When used as a control device, the invention also includes valve means operable in response to movement of the intermediate member, the valve means connecting the first diaphragm chamber directly to a supply of oxygen. Thus, when the oxygen pressure falls or the anesthesia gas pressure rises to move their ratio below the selected level, a bypass flow of oxygen is provided through the valve means, and the oxygen flow rate is effectively regulated and maintained above the desired percentage of flow rate, regardless of the selected flow rates for the gases.

In accordance with another aspect of the invention, means are included for overriding the regulator action of the invention to allow it to operate as an alarm only. More specifically, this override means includes a pneumatic switch in a line carrying the bypass flow of oxygen to the valve means. When the switch is closed, the system operates as a regulator and provides a supplementary flow of oxygen to guarantee a desired oxygen flow rate percentage. When the switch is open, no bypass oxygen flow can be obtained and the system operates purely as an alarm system. The switch is actuated by a single control button which not only makes and breaks the required pneumatic connection, but also effects electrical switching of an audible alarm, to provide different sounds when the regulator is in operation, and includes a mechanical interlock to prevent the operator from disabling regulator action easily or inadvertently. The switch also provides a conspicuous visual indication that the regulator action has been overriden.

In accordance with another aspect of the invention, means are provided for obtaining a desired oxygen percentage alarm signal even down to extremely low oxygen flow rates. More specifically, a variable anesthesia gas restrictor is employed, having a substantially linear pressure-flow characteristic even at flow rates well below one liter per minute. The variable restrictor includes a ball valve, a tapered seat, and an adjustable spring for biasing the ball valve into the tapered seat at low flows. When flows become extremely low, the restrictor further restricts the flow, as the ball is biased further into the tapered seat. For higher flows, flow pressure holds the ball away from the seat and compresses the spring. The resulting pressure-flow characteristic is practically linear down to extremely low flow rates. When the flow restrictor is used in conjunction with the low-oxygen alarm and control system of the invention, both the alarm and control system are actuated at a desired oxygen flow percentage, which remains constant even down to flow rates of approximately 100 milliliters of oxygen per minute.

In accordance with yet another aspect of the invention, the patient airway pressure is monitored for transitions through a selected threshold pressure in both directions. In this regard, the invention includes means for detecting a pressure transition through the threshold in an upward direction and means for detecting pressure transitions through the threshold in a downward direction, both of these means operating in conjunction with timing means for determining whether successive transitions of the same type occur within a preselected time period. In this manner, both disconnections and blockages of pneumatic lines are promptly detected and an alarm actuated.

It will be appreciated from the foregoing that the present invention represents a significant advance in the field of cas anesthesia machines. In particular, it provides a low-oxygen detection system that is not dependent on the adjustment of flow restrictors and that is operable down to extremely low flow rates. Moreover, the detector system can be used in conjunction with a control system to augment the oxygen flow rate automatically and thereby maintain it above a desired level. Means are included for overriding the control system in a manner which provides for convenient operation and conspicuous display when the override feature is activated. Other aspects and advantages of the invention will become apparent from the following more detailed description, taken in conjunction with the accompanying drawings.

DESCRIPTION OF THE PREFERRED EMBODIMENTS

Figure 1:
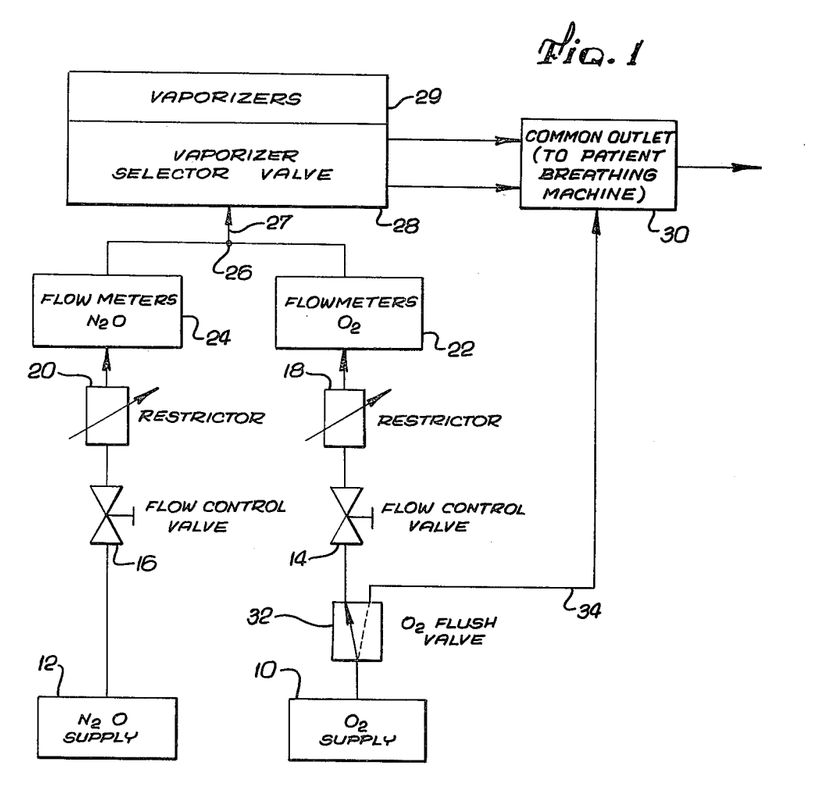
FIG. 1 is a simplified schematic view of a gas anesthesia machine.

As shown in the drawings for purposes of illustration, the present invention is concerned with alarm and control systems for use with gas anesthesia machines. FIG. 1 shows the basic configuration of a gas anesthesia machine, including an oxygen supply, indicated by reference numeral 10, a nitrous oxide suoply 12, oxygen and nitrous oxide flow control valves 14 and 16, respectively, oxygen and nitrous oxide flow restrictors 18 and 20 respectively, and oxygen and nitrous oxide flow meters 22 and 24, respectively. The gas supplies 10 and 12 are connected through the respective flow control valves 14 and 16, thence through the respective restrictiors 18 and 20 and through the respective flow meters 22 and 24. The gas flow from the flow meters 22 and 24 is then combined at a single manifold, as indicated at 26, and passed over line 27 to vaporizor selector valves indicated generally at 28, for connection to vaporizers 29 on a selected basis, and thence to a common outlet indicated at 30. The common outlet is connected to a patient breathing machine (not shown) which typically includes a carbon dioxide absorber and check valves to ensure that the patient inhales only from the common outlet and exhales only into the carbon dioxide absorber. The patient breathing machine may also include a ventilator to pump the nitrous oxide and oxygen into the patient's lungs, and a gas evacuation system for removing excess anesthesia gas from the patient breathing machine.

Also shown in FIG. 1 is an oxygen flush valve 32 connected in the oxygen supply line between the supply 10 and the control valve 14. The purpose of the flush valve 32 is to provide a means for diverting the oxygen flow, as shown by line 34, directly to the common outlet 30, for use in situations in which a pure oxygen flow is needed to flush the patient breathing machine.

In operating the simplified system shown in FIG. 1, an operator, who is usually a doctor, adjusts the flow control valves 14 and 16 until the desired gas flows are observed in the flow meters 22 and 24. However, there is always a danger that not enough oxygen will be supplied to the patient, and some means must be provided for actuating an alarm when the percentage of oxygen falls below a preselected level, typically around twenty-five or twenty-six percent of the total gas flow by volume.

In accordance with the invention, a novel gas flow gas detector and regulator assembly, indicated by reference numeral 36 (FIG. 2) is used either for alarm or control purposes, or both. The regulator assembly 36 includes a first chamber 38 defined in part by a first diaphragm 40, and a second chamber 42 defined in part by a second diaphragm 44. An intermediate member 46 is interposed between the first and second diaphragms 40 and 44 and has an upper surface practically co-extensive with the surface of the first diaphragm and a lower surface practically co-extensive with the surface of the second diaphragm. The intermediate member 46 is free to move axially with the two diaphragms 40 and 44 and is limited in movement only by the freedom of movement of the diaphragms themselves.

Figure 2:
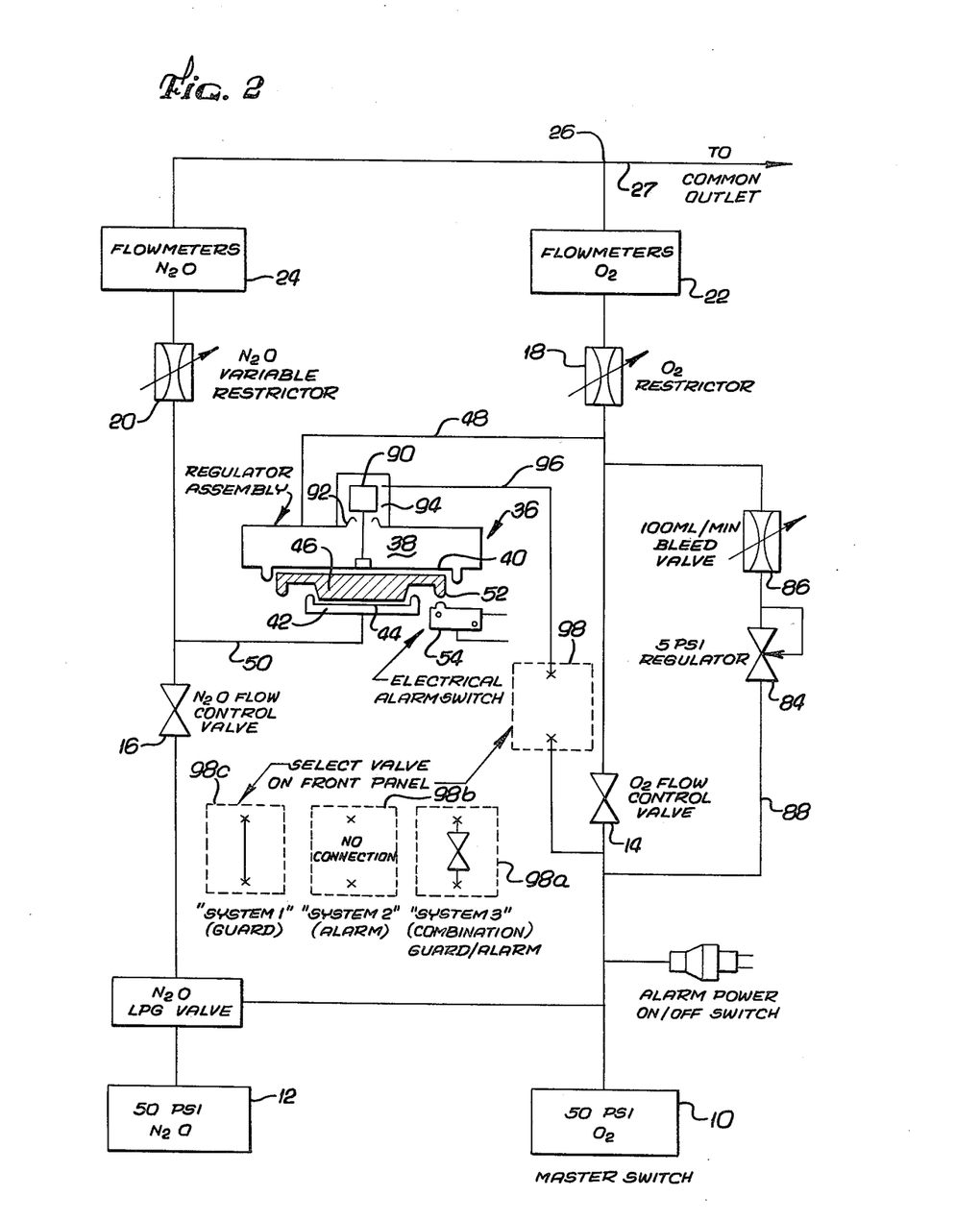
FIG. 2 is a schematic view similar to FIG. 1 but showing the low oxygen detection system of the invention used as both an alarm and as a control system.

The first chamber 38 has connected to it a line 48 extending from the oxygen supply line between the oxygen control valve 14 and the oxygen flow restrictor 18. Thus, the pressure of oxygen on the supply side of the flow restrictor 18 is applied to the first diaphragm 40. In similar fashion, a line 50 connects the nitrous oxide supply, between the flow control valve 16 and restrictor 20, to the second chamber 42, and the nitrous oxide pressure at the supply side of the flow restrictor 20 is applied to the surface of the second diaphragm 44.

In accordance with one important aspect of the invention, the first diaphragm 40 is approximately three times the area of the second diaphragm 44. Thus, the intermediate member 46 remains in a neutral position when a nitrous oxide pressure of approximately three times the oxygen pressure is applied to the second chamber 42. The intermediate member 46 has a lower surface considerably smaller in area than its upper surface and also has a peripheral flange 52 depending from its upper surface. This flange is used to actuate an electrical switch 54 for purposes of energizing an alarm. Since the diaphragms 40 and 44 have different surface areas, the flow restrictors 18 and 20 can be of substantially similar characteristics, and need be used only for purposes of fine tuning of the desired alarm level. Without the use of diaphragms of different areas, it would be necessary to obtain three times the pressure from the oxygen restrictor than from the nitrous oxide restrictor, or to bias the intermediate member 46 with springs.

Figure 3:
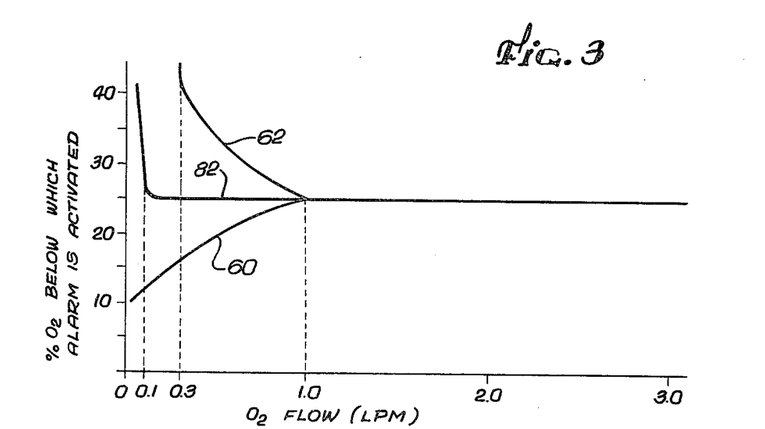
FIG. 3 is a graph showing the variation of detected percentage of oxygen and the oxygen flow rate.
Figure 4:
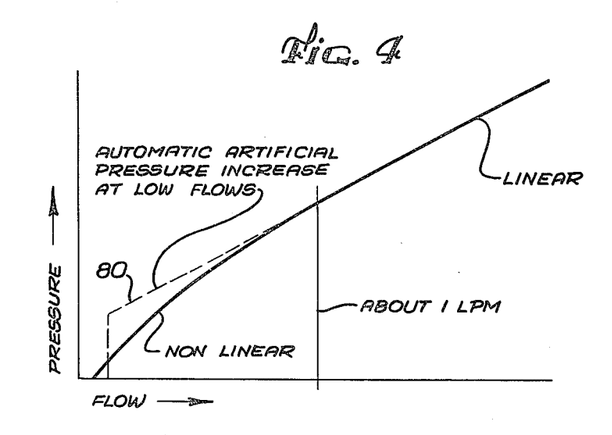
FIG. 4 is a graph showing the relationship between pressure and flow in a nitrous oxide flow restrictor.

As shown in FIG. 4, the relationship between the pressure on the supply side of the nitrous oxide restrictor 20 and the flow through the restrictor is non-linear below a certain flow rate. At low flow rates, the pressure drops off substantially below the desired linear relationship. This results in a characteristic indicated by reference numeral 60 in FIG. 3. Since the pressure from the nitrous oxide restrictor 20 is lower than it would be if the pressure-flow characteristic were linear, the regulator assembly 36 behaves as if the percentage of nitrous oxide was greater than it is in fact, and the percentage of oxygen was greater than it is in fact. Thus, the real percentage of oxygen at which the alarm is actuated falls below the desired level, and may drop as low as ten percent at extremely flow rates.

Clearly, this is an undesirable situation, but the only attempt to rectify it in the prior art has resulted in the curve shown at 62 in FIG. 3. Basically, what was done in the past was to spring-bias the ratio detection device in such a manner that, at low flow rates, spring pressure would be applied to the nitrous oxide side of the device, and the alarm would be actuated at real oxygen percentages higher than the desired value, perhaps as high as forty percent in some cases. Although this approach provides a desirable factor of safety, in the sense that an alarm is sounded at least some time before the oxygen level reaches the danger level, it nevertheless represents an inconvenience for the doctor, who may wish to work at oxygen levels below thirty to forty percent and can do so only by ignoring or suppressing the alarm condition. There is then an inherent danger that a real low-oxygen situation could occur subsequently and could go unnoticed if the alarm had been suppressed or was being deliberately ignored.

Figure 5A:
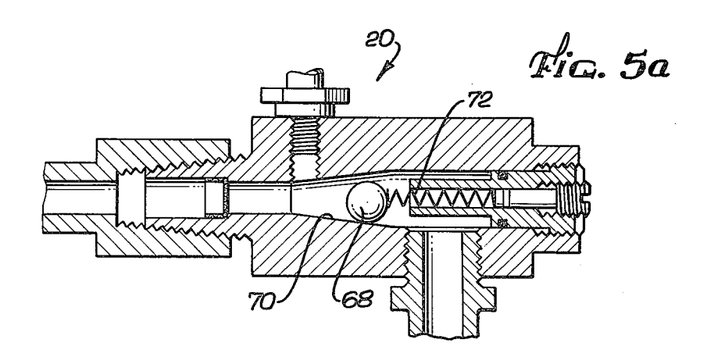
FIGS. 5a and 5b are longitudinal cross-sectional views showing the operation of the nitrous oxide variable flow restrictor of the invention.
Figure 5B:
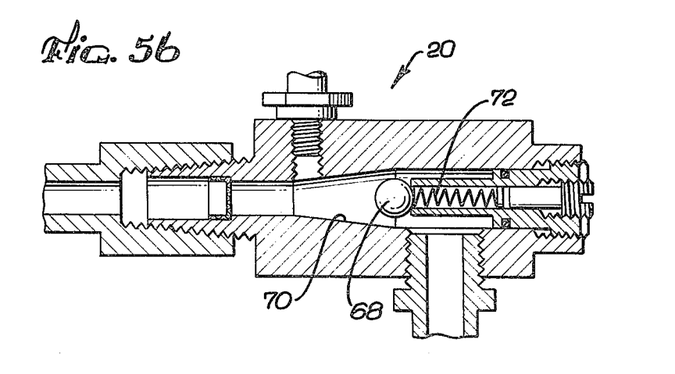

In accordance with another important aspect of the invention, the non-linearity of the pressure-flow characteristic of nitrous oxide is compensated for by means of the novel variable flow restrictor illustrated in FIGS. 5a and 5b. Basically, the restrictor 20 includes a ball valve 68, which may be partially seated in a tapered valve seat 70. The seat 70 is narrower at the supply end of the restrictor, i.e., gas flow is from the narrower end to the wider end. Also included is an adjustable compression spring 72 which, in conditions of low flow, biases the ball valve 68 into the tapered seat 70. The lower the flow rate, the further the ball 68 is biased into the tapered seat 70 and the greater is the restriction to flow. Thus, at low flow rates the increased restriction results in a higher pressure than in a conventional restrictor. At higher flow rates, however, the ball 68 is pushed against the spring 72, compressing it and allowing a relatively free flow through the restrictor. The resulting pressure-flow characteristic is shown at 80 in FIG. 4, and the resulting curve in FIG. 3 is shown at 82, indicating that the percentage oxygen level below which the alarm is actuated is maintained constant down to an extremely low level, perhaps as low as 100 millimeters per minute. In the system shown in FIG. 2, oxygen flows below 100 millimeters are not possible because of the incorporation of an additional regulator 84 and a bleed valve 86 connected in a separate line 88 bypassing the oxygen flow control valve 14.

Thus far in this description, the regulator assembly 36 has been discussed in terms of its function as an alarm device. Even if an alarm is indicated as shown in FIG. 3 whenever the oxygen level falls below twenty-five percent, the doctor may elect to ignore the alarm or to switch it off, or the alarm may be malfunctioning, in which case the oxygen percentage may continue to fall below the danger level. In many situations, therefore, it would be highly desirable to have a minimum percentage of oxygen guaranteed, regardless of the condition of the flow control valves 14 and 16. In accordance with this aspect of the invention, the regulator assembly 36 includes a valve 90 affixed to or bearing on the intermediate member 46 of the assembly, and a valve seat 92 forming an opening in the first chamber 38.

In operation, so long as the percentage of oxygen flow is sufficient to maintain the intermediate member 46 at or below its neutral position the valve 90 forms a closure in the seat 92, and the assembly operates in the manner already described. If, however, the oxygen flow rate falls sufficiently to actuate the alarm switch 54, shortly thereafter the valve 90 is lifted from the seat 92, thereby connecting the first chamber 38 with a valve chamber 94. The valve chamber 94 communicates with a line 96 connected through a device indicated at 98 to the oxygen supply line on the supply side of the control valve 14. For the device to operate as an oxygen regulator, the device 98 must be either a permanent fluid connection, or a pneumatic switch in the closed position.

When the valve 90 opens, oxygen is diverted through the valve chamber 94 into the first chamber 38, and thence over line 48 to the oxygen restrictor 18. In effect, the line 96, valve 90 and line 48 form a bypass circuit for the flow of oxygen. When the flow of oxygen is again sufficient to increase the pressure on the first diaphragm 40, the valve 90 closes. In this manner, the valve 90 and the remainder of the regulator assembly 36 operate to guarantee that the intermediate member 46 will be positioned at or above its neutral position, and that the oxygen flow rate will never fall below the desired value.

To facilitate manufacture of anesthesia machines meeting various requirements for oxygen regulation, the system may be made to include the device 98 either in the form a pneumatic switch, as shown at 98a, no connection at all, as shown at 98b, or with a permanent fluid connection, as shown at 98c. When the switch 98a is used, the system operates both as an optional ratio guard and as a ratio alarm. With no connection, as shown at 98b, the system operates purely as an alarm system, and with a solid connection, as shown in 98c, the system operates both as a guard and as an alarm, but without the option of overriding the guard system.

One aspect of the invention when used as a ratio guard and alarm system which is overridable by use of the pneumatic switch 98a, is that appropriate means are provided to ensure that the doctor is constantly aware of the override condition when this is elected. First, a different audible alarm is provided when the system is operating as an alarm, as compared with the audible alarm provided when the system is operating as a ratio guard. For example, when the system is operating as a ratio guard there is a flashing light and an audible signal of increasing volume and increasing frequency. However, when the system is operating only as a ratio alarm and not as a ratio guard, a fast wobble in frequency is also added to the audible signal, to call attention to the fact the system is not automatically supplementing the oxygen supply.

Another way that the invention provides a visual indication that the ratio guard feature has been overriden is by means of a control switch used to effect overriding. As shown in FIGS. 11-16, a push-button control 100 is used to oparate the pneumatic switch 98a. Although the control 100 appears to be a simple push-button switch, in fact it performs three distinct functions simultaneously. First, it closes the pneumatic switch 98a to connect the oxygen line 96 between the oxygen supply 10 and the regulator assembly 36. Secondly, actuation of the switch effects the necessary electrical connections to change the audible alarm as previously described. Thirdly, the push-button control 100 is so constructed that it cannot be placed in the off position without first lifting an access cover 102, which will then be held in the lifted position so long as the switch is in the off position. Moreover, when the access cover 102 is lifted it exposes cautionary signs indicating that the ratio guard has been overridden. Thus, the single push-button control 100 provides pneumatic connection, electrical connection, and a mechanical display of a warming sign behind the access cover.

Figure 11:
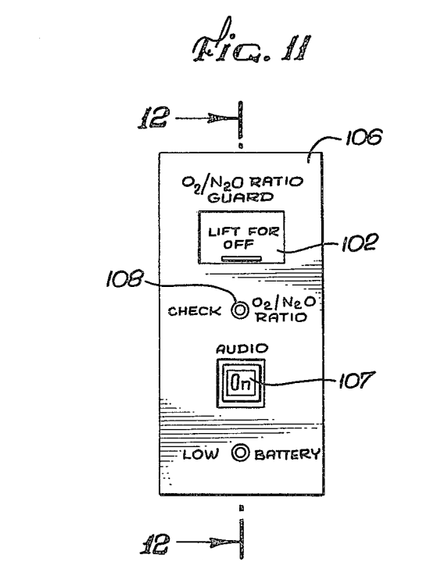
FIG. 11 is a front elevational view of a switch panel for overriding the oxygen regulator of the invention.

More specifically, the push-button control 100 is mounted in a panel 106, together with an audio alarm switch 107 for silencing the alarm. The alarm system cannot be completely disabled by switch 107, however. A warning light 108 will continue to flash, and the audible alarm will sound every half minute. Also, new alarm conditions override the alarm-off switch for a few seconds.

Figure 15:
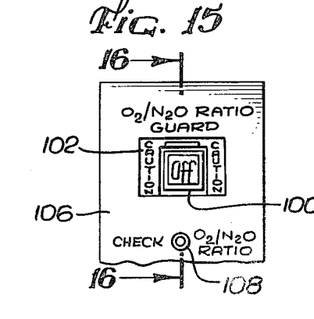
FIG. 15 is a fragmentary front view of the switch panel with the switch in the off position.
Figure 16:
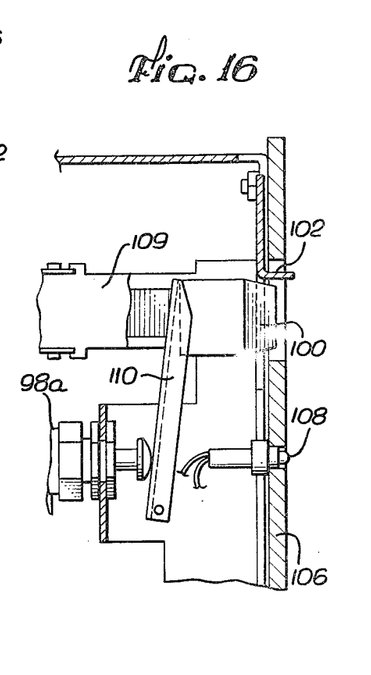
FIG. 16 is a sectional view taken substantially along the line 16—16 in FIG. 15.

The push-button control 100 is part of a commercially available electrical switch 109 used to control the audible alarm and provide an electrical signal indicative of the ratio guard condition. The switch 109 is operated by pushing and releasing the control 100, both for switching on and for switching off. In the on condition, however, the control 100 is held behind the panel 106, and the access cover 102 can close under its own weight, to prevent inadvertent operation of the switch. When the cover 102 is lifted and the control 100 actuated to switch to the off condition, the control extends part of the way through the panel 106 to prevent the cover from closing, as shown in FIGS. 15 and 16.

Figure 12:
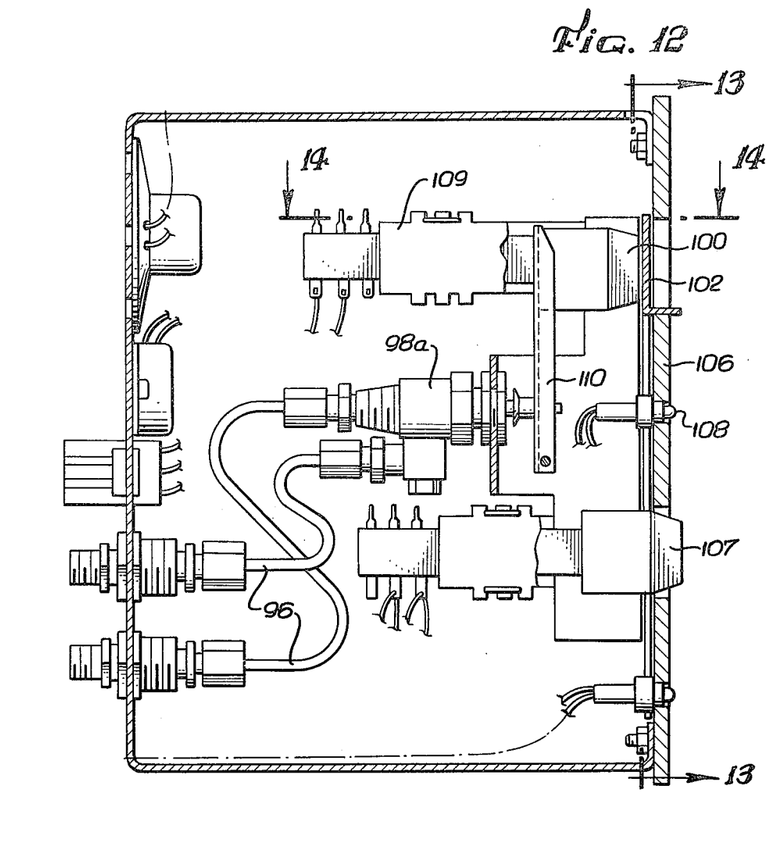
FIG. 12 is a sectional view taken substantially along the line 12—12 in FIG. 11.
Figure 13:
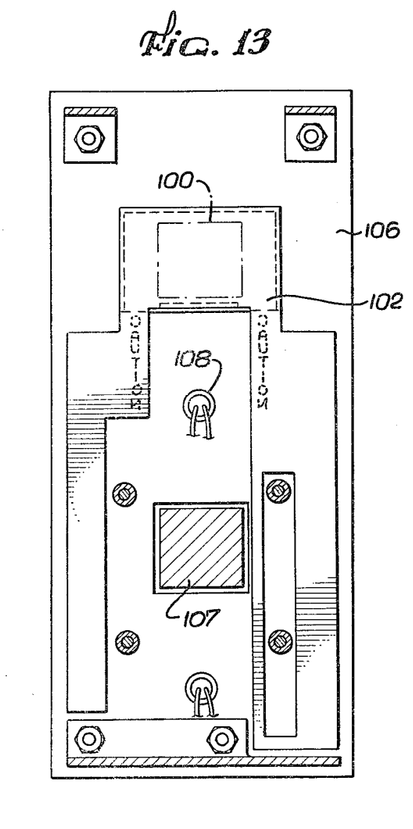
FIG. 13 is a rear view, partly in section, taken substantially along the line 13—13 in FIG. 12.
Figure 14:
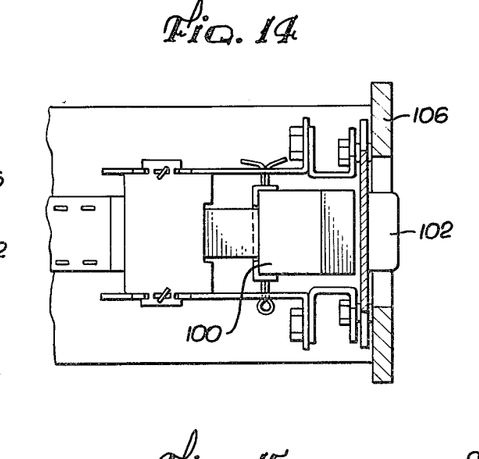
FIG. 14 is a plan view, partly in section, taken substantially along the line 14—14 in FIG. 12.

Movement of the push-button control 100 is coupled to the pneumatic switch 98a by a lever 110. The lever is pivoted below the switch 98a, coupled to the push-button at the lever's upper end, and engages a spring-biased plunger 111 that operates the pneumatic switch. Movement of the push-button 100 to the on position, depresses the plunger 111 and closes the pneumatic switch 98a.

Figure 6:
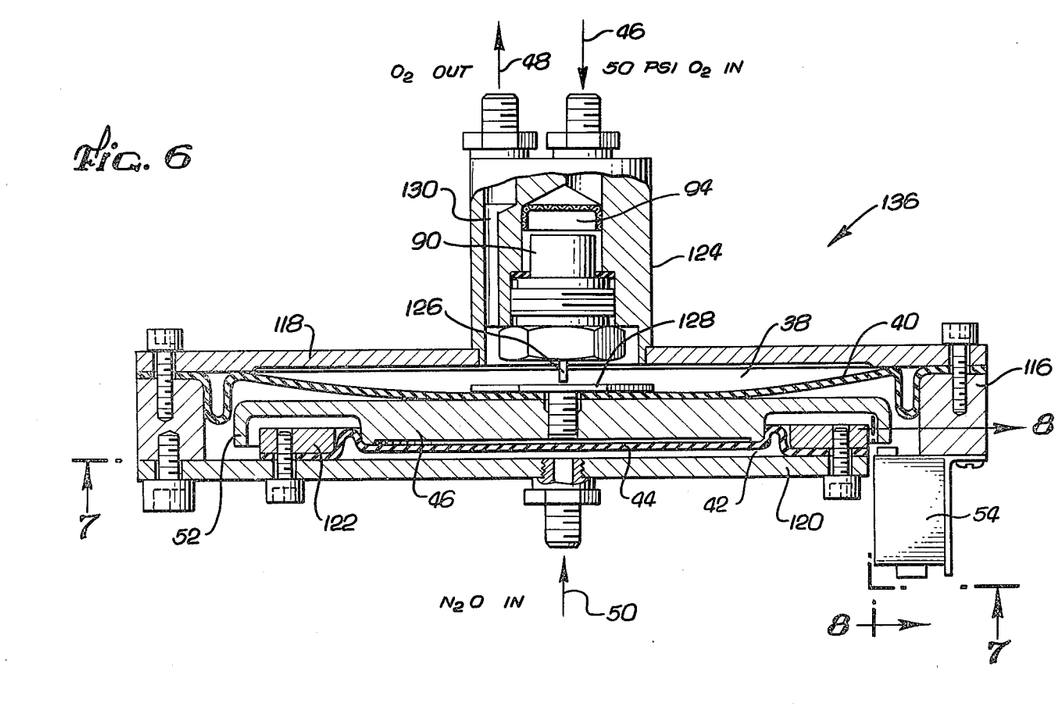
FIG. 6 is a cross-sectional view of the regulator assembly of the invention.
Figure 7:
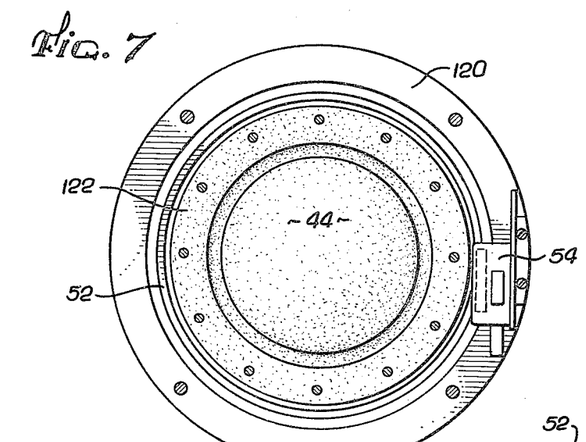
FIG. 7 is a bottom plan view, partly in section, of the regulator assembly.
Figure 8:
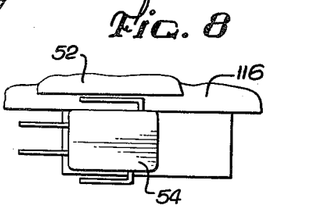
FIG. 8 is a sectional view taken substantially along the line 8—8 in FIG. 6.

The regulator assembly 36 (FIG. 2) is shown in more detail in FIGS. 6–8. The assembly 36 includes an outer annular ring 116 to which are secured an upper cover plate 118 and a lower cover plate 120. The first diaphragm 40 is secured about its circumference between the upper cover plate 118 and the ring 116. A second annular ring 122 is employed to secure the second diaphragm 44 to the lower cover plate 120. A cylindrical body 124 at the center of the top cover plate 118 encloses the valve chamber 94 and valve 90. A valve actuating stem 126 projects downwardly into the chamber 38, and, when the oxygen flow rate falls to too low a level, the stem is contacted by a strike plate 128 secured to the intermediate member 46. Oxygen line 48 communicates with the chamber 38 through a passage 130 near the outside of the cylindrical body 124.

Figure 9:
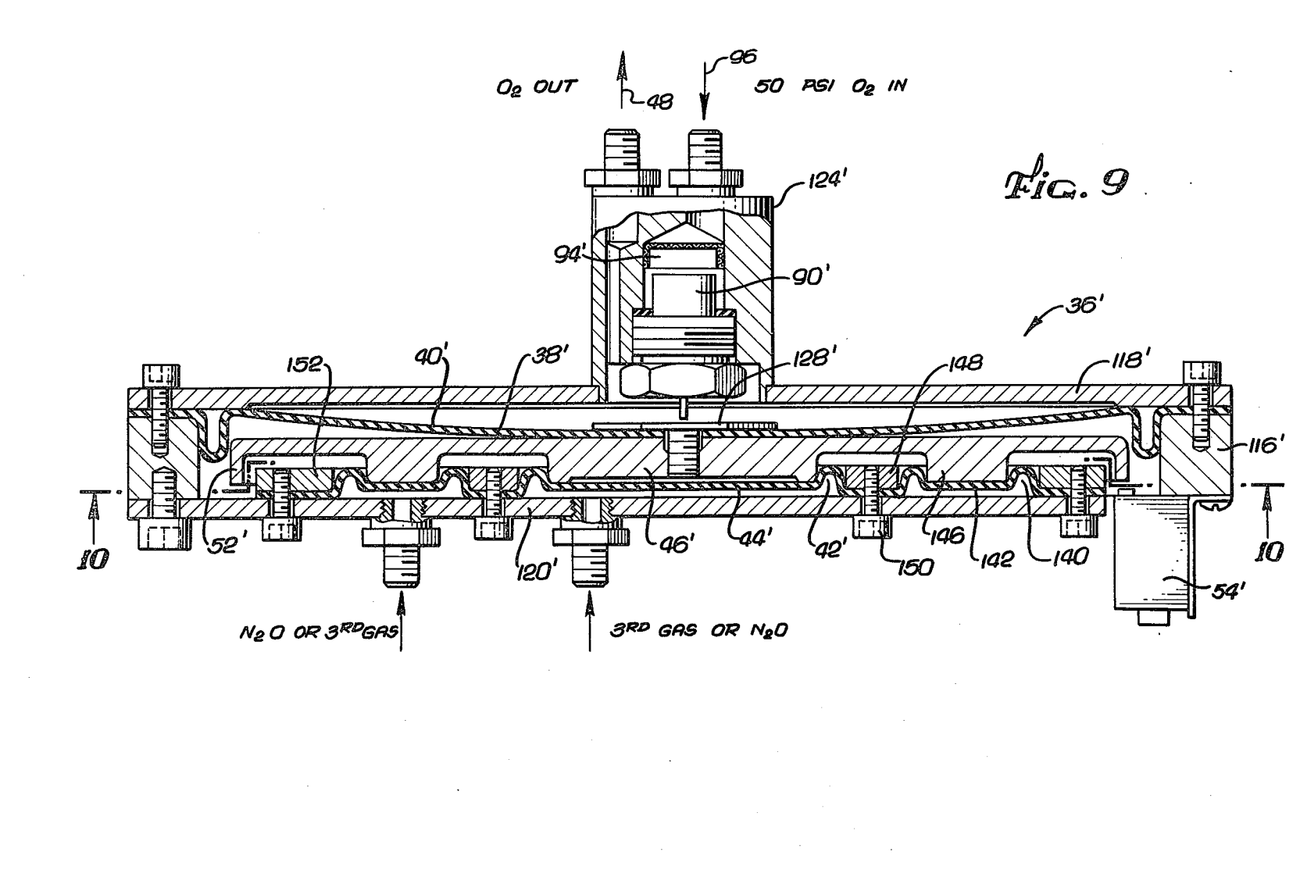
FIG. 9 is a cross-sectional view of an oxygen ratio alarm for oxygen and two other gases.
Figure 10:
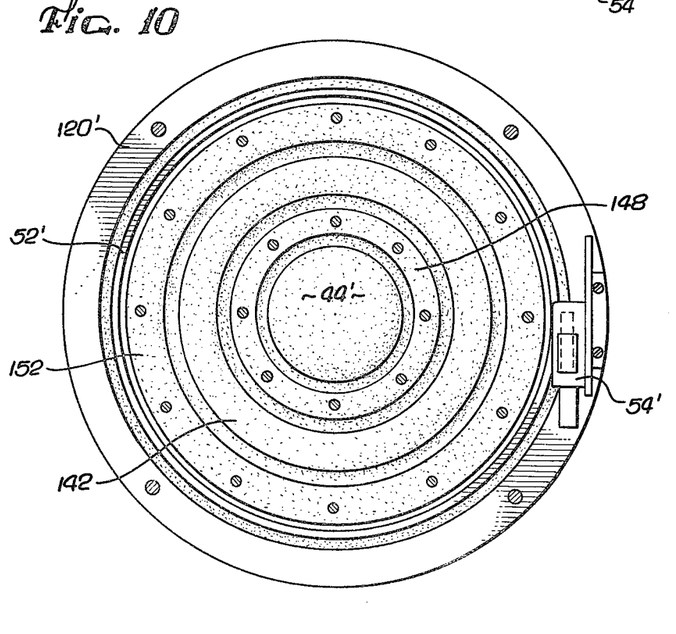
FIG. 10 is a bottom plan view of the regulator assembly of FIG. 9.

The concept described with respect to the regulator assembly is not limited to the use of oxygen and nitrous oxide or even to the use of two gases. FIGS. 9 and 10 show an example of a regulator assembly 36' operating on similar principles to regulator assembly 36 but providing a ratio alarm for oxygen, nitrous oxide and a third gas. It is similar in construction in that there is a first chamber 38', a second chamber 42', a first diaphragm 40' and a second diaphragm 44'. The regulator assembly 36' also includes an intermediate member 46' having an upper surface practically co-extensive with the first diaphragm 40' and having a lower surface of which a central portion is co-extensive with the second diaphragm 44'. The regulator 36', however, also includes a third chamber 140 which is annular in shape, surrounding the second chamber 42' and includes a third diaphragm 142, also annular in shape and positioned in the third chamber. The intermediate member 46' includes an annular protrusion 146 having a surface area practically co-extensive with the third diaphragm 142. As shown in the drawings, the second and third diaphragms 44' and 142 can be made of a single piece of material, separation being made at an annular sealing ring 148 secured by screws 150 as shown. An outer sealing ring 152 secures the outer circumference if diaphragm 142 to the lower cover plate 120.

Nitrous oxide and a third gas are placed in fluid communication with the second and third chambers, it being of little consequence whether the nitrous oxide as applied to the second or the third chamber. In any event, the oxygen pressure applied to the first chamber is balanced by the pressure of the nitrous oxide and the third gas applied to the second and third chambers. Consequently, the device operates as an oxygen ratio alarm in the same manner as the regulator assembly 36. The valve 90' and related structure are basically the same as in the assembly 36. It will be apparent that the regulator assembly 36' could be expanded to include means for obtaining a ratio alarm or regulator for any combination of gases.

Figure 17:
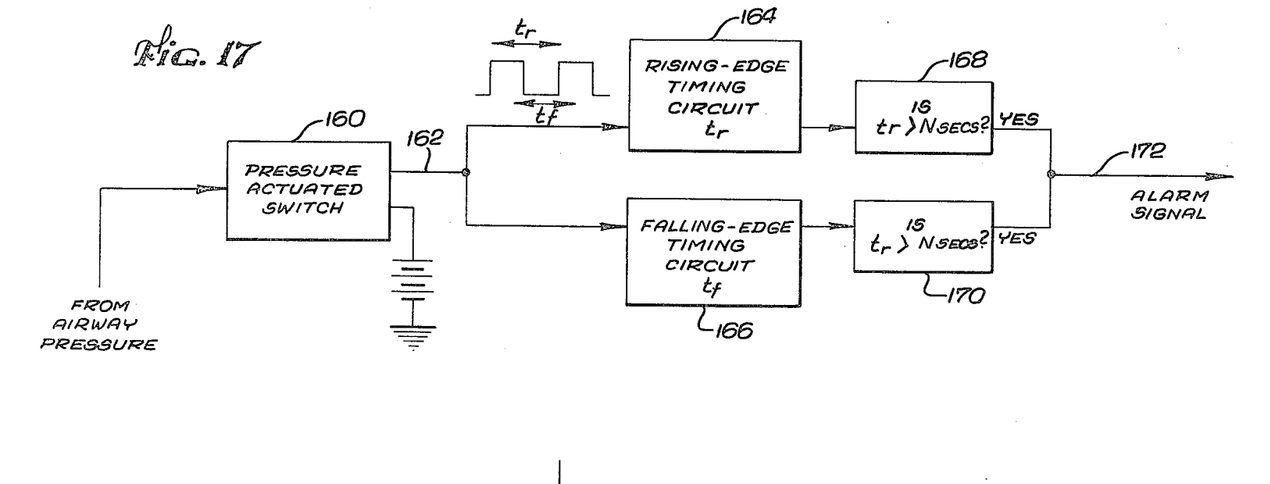
FIG. 17 is a simplified schematic diagram of apparatus for providing an alarm siznal when the patient airway pressure fails to pass through a selected threshold within a selected time.
Figure 18:
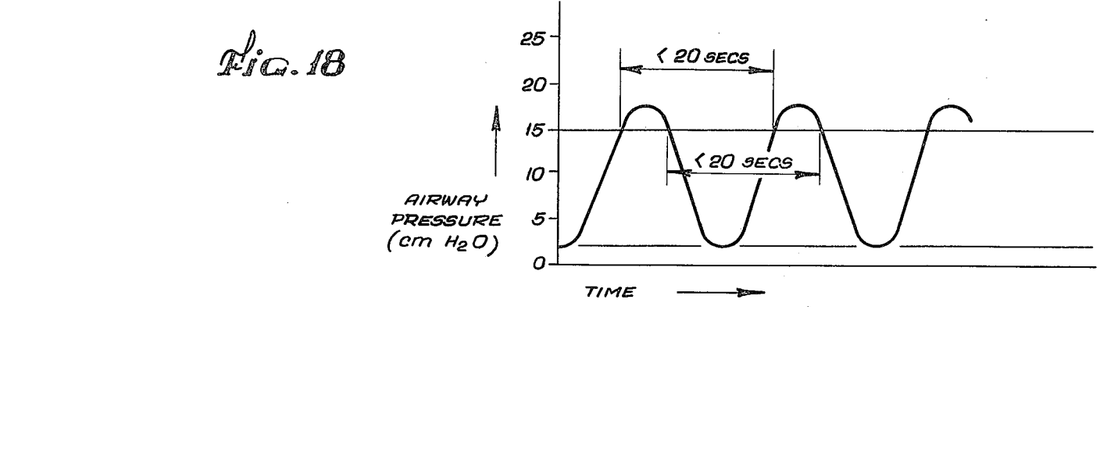
FIG. 18 is a graph showing a typical cyclic variation of pressure in the patient airway.

As shown in FIG. 18, the patient airway pressure typically varies in a cyclic fashion when the patient is breathing normally, and monitoring this cyclic pressure variation is often used as a means for providing a ventilator alarm indicative of a break or disconnection in the patient breathing system. In accordance with this aspect of the invention, a pressure actuated switch, indicated at 160, is provided with pressure from the patient airway, and is typically adjustable to select a desired threshold pressure. One switch that could be used, for example, is one of the type described in U.S. Pat. application Ser. No. 232,839, filed on Feb. 9, 1981, entitled "Adjustable Pressure-Actuated Switch" and assigned to the same assignee as the present application.

The pressure-actuated switch 160 provides a signal on line 162 indicative of whether the airway pressure is above or below the selected threshold level. This switch signal is transmitted to a rising-edge timing circuit 164 and to a falling-edge timing circuit. The rising-edge timing circuit measures the time $t_r$ between successive rising edges of the signal obtained from the pressure actuated switch 160. Similarly, the falling-edge timing circuit 166 measures the time $t_f$ between successive falling edges of the signal from the pressure-actuated switch 160. As shown at block 168, the time $t_r$ is compared with a selected value of N seconds, and in block 170, the time $t_f$ is also compared with the value N seconds. As indicated at 172, if either if these times exceeds the selected time interval, an alarm signal is generated. If the airway pressure does not rise above the selected value within the selected time interval, typically about 20 seconds, it is assumed that there is a break or disconnection in the patient breathing system. Similarly, if the pressure does not fall below the selected threshold level within the selected time interval, it is assumed that there is a blockage in the patient breathing machine.

It will be appreciated from the foregoing that the present invention represents a significant advance in the field of gas anesthesia machines, and in particular in the field of alarm and regulator systems for such machines. By way of summary, the invention provides an oxygen ratio alarm system capable of operating as an alarm at a selected percentage level down to extremely low flow rates, and as an oxygen ratio guard system to maintain a selected ratio of oxygen to nitrous oxide, regardless of the flow control valve settings. In addition, the invention provides for an improved ventilator alarm capable of detecting blockages as well as breaks and disconnections in the patient breathing system. It will also be appreciated that, although specific embodiments of the invention have been described in detail for purposes of illustration, various modifications may be made without departing from the spirit and scope of the invention. Accordingly, the invention is not to be limited except as by the appended claims.

I claim:

1. An oxygen regulator and alarm system for use in conjunction with a gas anesthesia machine, said system comprising:
   a regulator assembly having
   a first chamber,
   a first diaphragm serving as a wall of said first chamber,
   a second chamber,
   a second diaphragm serving as a wall of said second chamber,
   an intermediate member disposed between and in contact with said first and second diaphragms and movable therewith, and
   an alarm switch operable by movement of said intermediate member;
   an oxygen flow restrictor connected between a flow controllable oxygen supply and a common outlet;
   an anesthesia gas flow restrictor connected between a flow controllable supply of anesthesia gas and the common outlet;
   an oxygen pressure line between the supply side of said oxygen flow restrictor and said first chamber;
   an anesthesia gas pressure line between the supply side of said anesthesia gas flow restrictor and said second chamber; and
   an oxygen bypass line for connecting said first chamber directly to a supply of oxygen;
   wherein the area of said diaphragm is greater than the area of said second diaphragm by a factor sufficient to provide equal pressure forces on said diaphragms when the percentage flow rate of oxygen is at a desired safety level;
   and wherein said regulator assembly further includes a regulator valve for controlling the flow of oxygen into said first chamber from said oxygen bypass line, in response to movement of said intermediate member, whereby a too low percentage of oxygen causes said regulator valve to open, increasing the oxygen pressure in said first chamber and supplying additional oxygen to the common outlet through said oxygen bypass line, said first chamber and said oxygen pressure line.

2. An oxygen regulator and alarm system as set forth in claim 1, and further including a pnuematic switch in said oxygen bypass line, for overriding operation of said system as a regulator.

3. An oxygen regulator and alarm system as set forth in claim 1, wherein:
   said pneumatic switch is operable by a single pushbutton control;
   said pushbutton control also actuates an electrical switch to provide different audible alarm signals during regulator operation and overriden operation;
   said system includes an access cover over said pushbutton control; and
   said pushbutton control can be placed in an override position only by first raising said access cover, which remains raised while regulator operation is overriden and provides a visual indication of the override condition.

4. An oxygen regulator and alarm system as set forth in claim 1, wherein said anesthesia gas flow restrictor includes compensation means for providing a practically linear pressure-flow characteristic at extremely low flow rates of the anesthesia gas.

5. An oxygen regulator and alarm system as set forth in claim 4, wherein said compensation means includes:
   a flow restrictor passage with a region tapered in diameter;
   a ball sized to be seated in said tapered region; and
   an adjustable spring for biasing said ball into said tapered region in conditions of low flow, thereby producing a higher pressure at low flows to compensate for non-linearity in the pressure-flow characteristic of said restrictor.

6. A low-oxygen-detection and oxygen regulation system for use in conjunction with a gas anesthesia machine, said system comprising:
   a first chamber, to which oxygen is supplied;
   a first diaphragm serving as a wall of said first chamber;
   a second chamber, to which anesthesia gas is supplied;
   a second diaphragm serving as a wall of said second chamber;
   an intermediate member disposed between and in contact with said first and second diaphragms, and movable with said diaphragms in response to differences in force applied to said diaphragms by the gases in said chambers;
   alarm actuation means operable by movement of said intermediate member;
   oxygen flow restrictor means having its inlet side connected to said first chamber; and
   anesthesia gas flow restrictor means having its inlet side connected to said second chamber;
   wherein said first diaphragm is larger in area than said second diaphragm by a factor sufficient to provide equal pressure forces on said diaphragms when the percentage flow rate of oxygen is at a desired safety level;
   and wherein said flow restrictors provide sufficient pressure to operate said low-oxygen detection system, and may be used to make fine adjustments to the level at which said alarm actuation means is actuated;
   and wherein said system further includes an oxygen supply line for connecting said first chamber directly to a supply of oxygen, and valve means connecting said first chamber to said oxygen supply line and operable in response to movement of said intermediate member toward said first chamber beyond a preselected point, whereby detection of an oxygen flow rate percentage below the safety level opens said valve means and provides a supplementary flow of oxygen through said valve means to said first chamber.

7. A low-oxygen detection system as set forth in claim 6, wherein said valve means includes:
   an opening into said first chamber; and
   a valve seatable in said opening and having a valve stem extending into said first chamber toward said first diaphragm;
   whereby movement of said first diaphragm into said first chamber beyond a preselected point results in movement of said valve stem and opening of said valve.

8. A low-oxygen detection system as set forth in claim 6 or 4, and further including means for overriding operation of said system as an oxygen regulator.

9. A low-oxygen detection system as set forth in claim 8, wherein said means for overriding operation of said system as an oxygen regulator includes a pneumatic switch in said oxygen supply line, whereby opening said pneumatic switch and blockage of said oxygen supply line causes said system to operate only in an alarm mode.

10. A low-oxygen detection system as set forth in claim 9, wherein said means for overriding operation of said system as an oxygen regulator also includes:
electrical switch means operable simultaneously with said pnuematic switch, to provide distinctly different alarm sounds when oxygen regulation is overriden; and
means for visually indicating that oxygen regulation has been overriden.

11. A low-oxygen detection system as set forth in claim 10, wherein said means for visually indicating that oxygen regulation has been overriden includes an access cover that must be lifted to actuate said means for overriding regulator operation, said access cover remaining open after overriding, to expose a reminder sign indicating overriding of regulator operation.

* * * * *